(12) United States Patent
Cipriani et al.

(10) Patent No.: US 9,486,642 B2
(45) Date of Patent: Nov. 8, 2016

(54) BRACHYTHERAPY METHOD OF TREATING SKIN TUMORS USING A TAILOR-MADE RADIOACTIVE SOURCE

(75) Inventors: Cesidio Cipriani, Rome (IT); Maria Desantis, Rome (IT)

(73) Assignee: ONCOBETA INTERNATIONAL GMBH, Ravensburg (DE)

( * ) Notice: Subject to any disclaimer, the term of this patent is extended or adjusted under 35 U.S.C. 154(b) by 409 days.

(21) Appl. No.: 13/025,703

(22) Filed: Feb. 11, 2011

(65) Prior Publication Data
US 2011/0201866 A1 Aug. 18, 2011

(30) Foreign Application Priority Data

Feb. 15, 2010 (AU) ................ 2010200556

(51) Int. Cl.
*A61N 5/00* (2006.01)
*A61N 5/10* (2006.01)

(52) U.S. Cl.
CPC ........... *A61N 5/1028* (2013.01); *A61N 5/1029* (2013.01)

(58) Field of Classification Search
CPC ............. A61K 8/0208; A61K 9/7084; A61K 9/7092; A61L 15/44; A61N 5/1001–5/1025; A61N 5/1028–5/1029
USPC ........... 600/1, 2, 8; 424/1.11, 1.25, 443, 447
See application file for complete search history.

(56) References Cited

U.S. PATENT DOCUMENTS

| | | | |
|---|---|---|---|
| 4,946,435 A | 8/1990 | Suthanthiran et al. | |
| 5,030,195 A | 7/1991 | Nardi | |
| 5,871,708 A | 2/1999 | Park et al. | |
| 5,871,823 A * | 2/1999 | Anders et al. | 427/512 |
| 6,350,226 B1 | 2/2002 | Fischell et al. | |
| 6,391,279 B1 * | 5/2002 | Singh et al. | 424/1.29 |
| 6,475,644 B1 | 11/2002 | Hampikian et al. | |
| 6,589,502 B1 * | 7/2003 | Coniglione et al. | 424/1.25 |
| 6,749,553 B2 | 6/2004 | Brauckman et al. | |
| 8,246,978 B2 * | 8/2012 | Kydonieus et al. | 424/448 |
| 2003/0180341 A1 * | 9/2003 | Gooch et al. | 424/401 |
| 2004/0116907 A1 * | 6/2004 | Tartaglia | A61B 19/54 606/1 |
| 2006/0206171 A1 | 9/2006 | Gertner et al. | |

OTHER PUBLICATIONS

Salgueiro, M.J., Duran, H., Palmieri, M., Pirchio, R., Nicolini, J., Ughetti, R., Papparella, M.L., Casale G., Zubillaga, M., "Design and bioevaluation of a 32P-patch for brachytherapy of skin diseases," 2008, Applied Radiation and Isotopes (66): 303-309.*
Bolderston, A., Lloyd, N.S., Wong, R.K.S., Holden, L., Robb-Blenderman, L., "The prevention and management of acute skin reactions related to radiation therapy: a systematic review and practice guideline," Support Care Cancer (2006) 14: 802-817.*

* cited by examiner

*Primary Examiner* — Catherine B Kuhlman
(74) *Attorney, Agent, or Firm* — Saliwanchik, Lloyd & Eisenschenk

(57) ABSTRACT

Embodiments of the invention relate to a method of treating a cancerous or non-cancerous skin lesion of a subject, e.g. a human patient, by epidermal radioisotope therapy, a specialized type of brachytherapy. The method can include defining and marking an area of skin to be treated; covering the area with a protective layer, e.g. a protective film or foil; applying a tailor-made radioactive source by applying a layer of a radioactive source material on the protective layer, such that the area is covered by the material while any area not to be treated is spared; and removing the radioactive source after a predetermined time period of irradiation.

30 Claims, 1 Drawing Sheet

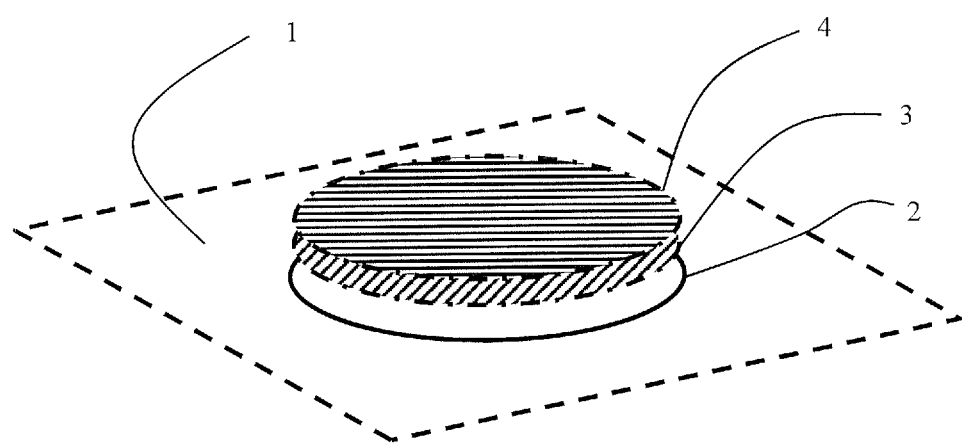

BRACHYTHERAPY METHOD OF TREATING SKIN TUMORS USING A TAILOR-MADE RADIOACTIVE SOURCE

CROSS-REFERENCE TO RELATED APPLICATION

The present application claims priority under 35 U.S.C. §119(a) of Australian Patent Application No. 2010200556, filed on Feb. 15, 2010, which is hereby incorporated by reference in its entirety, including any figures, tables, or drawings.

FIELD OF THE INVENTION

The present invention refers to a brachytherapy method of treating a tumor skin lesion, preferably a basal cell carcinoma or a squamous cell carcinoma, comprising the step of applying to an area of skin to be treated a tailor-made radioactive source comprising a matrix-forming component, preferably an acrylic resin, and a radioactive isotope, preferably a beta emitter isotope, on a film or foil covering said area in order to protect the skin from radioactive contamination.

BACKGROUND OF INVENTION

Skin cancer is the most common form of cancer in humans, and in some countries it accounts for about half of all tumors. Among all tumors of humans, basal cell carcinoma (BCC) is the most common cancer of white populations, and constitutes the 80% of the cases of skin cancer. BCC is a slowly-growing, locally invasive malignant epidermal skin tumor; it tends to infiltrate and destroy contiguous tissues, but metastatic diffusion is extremely rare. In the initial forms a superficial translucent nodule, waxen or grey-pearly color, or a pink or red spot with scarce abnormal blood vases, are often present. The most advanced forms show ulceration, particularly in central zone, and peripheral borders, in relief. It can appear in every part of the body, but 90% of the lesions appear in the face and on the head. BBC most frequently occurs in light-skinned, middle aged to old patients, with a history of ultraviolet exposure, but may also arise in basal cell nevus (Gorlin's syndrome). Australia has the highest rate of BCC in the world, and certain regions have an incidence of up 2% per year. Once a person has developed a BCC, there is a significantly increased risk of developing subsequent BCC's at other sites. Evidence suggests that BCC may arise from the multi-potent cells in the basal layer or follicles of the skin. There are several different histological and pathological clinical forms of BCC, but traditional diagnostic methods do not provide enough information on tumor features.

Squamous cell carcinoma (SCC) is an epithelial malignancy with morphologic features of squamous cell differentiation, without additional features suggestive of other differentiated tissues. It can appear in every part of the body, and can also develop on lips, vulva and penis; often it originates from burn scars or skin ulcers, and appears as a superficial lesion, that easily bleeds. Sometimes an ulceration develops, with thick crater-like borders; in other cases the lesion is covered by an horny layer. Other variants of skin cancers that originate from the cells of the superficial layer are represented by a particular SCC in-situ, called Bowen's disease, and by the "erythroplasia of Queyrat", a superficial form of in-situ SCC of male genitals. A particular form of SCC is the keratoacanthorma, in which a bulge or thick mass, often ulcerated, is formed in the parts of the body exposed to the sun. Finally, also the common actinic keratosis is today considered, in dermatology, an initial form of carcinoma in-situ. SCC is the second most common form of skin cancer, with over 200,000 new cases per year reported in the United States. The highest incidence occurs in Australia, where the age-adjusted incidence has been calculated to be 1332 cases per 100,000 population for men, and 755 cases per 100,000 population for women. In European countries, the annual rate of incidence of SCC is actually of about 25 cases per 100,000 people. SCC of the skin may metastasize to regional lymph nodes and is often locally recurrent.

The incidence of both BCC and. SCC increases with age, begins after the age of 30 years, peaks at the age of 65-70 years, and occurs more often in men than in women. Both tumors appear most frequently on the face, neck, bald scalp, hands, shoulders, arms and back; the rim of the ear and the lower lip are especially vulnerable to these cancers. The clinical appearances and morphology of both tumors are diverse, including nodular, cystic, ulcerated ('rodent ulcer'), superficial, morphoeic (sclerosing), keratotic and pigmented variants. Ulceration is especially common in large tumors, in long-standing or aggressive lesions. The risk factors include sun exposure, exposure to ionizing radiation, arsenic exposure, coal tar derivates and ultraviolet A radiation exposure. It is also recognized the importance of commonly predisponent factors, like immunosuppression, and physical characteristics, as fair complexion, red or blond hair, and light eye color.

BCC is characterized by a non-aggressive behavior, given its low metastatic potential (0.03 to 0.6%), but metastases have been described in the subcutaneous tissue, bones, lungs, liver, lymph nodes of the neck. SCC has a more aggressive behavior, and metastatic potential is higher (2% to 5%), but in some forms (like invasive Bowen, desmoplastic SCC, malignant proliferating pilar tumor/cyst, de-novo SCC, adenosquamous cell carcinoma, SCC arising from radiation, burn scars, cronic conditions or immunosuppresion) this risk raises to 10% and more.

The data furnished by the patient, and the objective examination of the lesions by an experienced dermatologist is of fundamental importance for a correct diagnosis. Nevertheless, only the microscopic (histology/cytology) examination can furnish the exact characterization and classification. The collecting of the tissue can be performed by surgical excision or by /biopsy through a special metallic punch (biopsy punch); sometimes a simple cytological examination of the scarified lesion is sufficient to confirm the diagnosis. The dermoscopic epiluminescence, largely employed for the diagnosis of pigmented lesions, allows the observation of characteristics features and of the vascular network to the lesion; the observation of the neoangiogenesis that characterizes the cancer lesion usually furnishes useful elements of judgment on the extension and depth of the lesion. For SCC, due to the high risk of metastatic diffusion, an accurate periodical examination of the patients is mandatory.

Clinical exams include a full body skin examination, palpation of previous excision sites and examination of the skin between primary tumor sites and draining lymph nodes for in-transit metastasis. Regional lymph nodes should be palpated for lymphadenopathy and any suspicious lymph node enlargement should be evaluated by biopsy, imaging, or both. Imaging techniques using CT or CT/PET are useful for staging and detecting distant disease. MRI provides superior resolution of soft tissue tumors, particularly in the head and neck region and should be considered for metastases that occur in these regions. Sentinel lymph node localisation and lymphoscintigraphy by $^{99m}$Tc colloid should be included, before and after therapy, of all suspect cases. Characteristics or primary tumors that develop into metastatic SCC include area >120 mm$^2$, invasion to a depth >3.2 mm, and invasion of underlying fat, muscle or bone.

The surgery practice is widespread performed, with margins of 2-4 mm recommended for nodular, well delineated, tumors sized up to 2 cm; for those larger than 2 cm, excision with margin of 1 cm, or more, is usually suggested, especially for tumors with aggressive course. Mobs' technique offers the best chances for cure and maximally preserves healthy tissue; it consists in the progressive histological real-time examination of tissue sections of the lesion during the surgery, up to the reaching of the healthy tissue.

In all cases in which tumors are located in areas on which surgery excision may be very difficult (ear, nose, eyelids), the aesthetic and functional results are often highly unsatisfactory. When the lesion is rather large, and the residual healthy skin is not sufficient for a satisfactory surgical suture, it is necessary to proceed to a plastics reconstructive surgery, with transplantation of healthy skin (usually from the inferior limb or from the gluteus skin). The cosmetic outcome is often unsatisfactory; if a relapse raises in transplanted skin, the management of the lesions becomes highly problematic. For both tumors, standard therapies like curettage and electrodessication, surgery, cryosurgery, and intralesional interferon therapy are often proposed to the patients. New alternative topical therapy are now available for the treatment of selected cases, such as tumors located in critical, or inoperable patients, owing to systemic underlying diseases (cardiomyopathy, pulmonary insufficiency). They include imiquimod, an immune response modifier used for the treatment of superficial BCC less than 2 cm in diameter, tazarotene, a retinoic acid, generally used for topical treatment of psoriasis, and proposed for the local treatment of BCC, photodynamic therapy, which involves the administration of a tumor-localizing photosensitizing agent and its subsequent activation with visible light to cause selective destruction of the tumor. The use of imiquimod cream was an effective treatment option for superficial and nodular basal cell carcinomas, giving a clearance rate of 89.5% at an average of 39 months of follow up (Vun Y, Siller G, Australas J Dermatol. 2006 August; 47(3):169-71). The use of photodynamic therapy with porfimer sodium at 1 mg/kg produced, at 5-year, recurrence rates of 28% and 15% for sporadic and nevoid basal cell carcinoma syndrome (NB-CCS) lesions, respectively (Oseroff A R, Blumenson L R, Wilson B D, Mang T S, Bellnier D A, Parsons J C, Frawley N, Cooper M, Zeitouni N, Dougherty T J, 2006 June; 38(5):417-26). By the use of meso-tetra-hydroxyphenylchlorine (m-THPC) mediated photodynamic therapy, good cosmetical results, with little or no scarring, were obtained in 87% of the treated lesions (Triesscheijn M, Ruevekamp M, Antonini N, Neering H, Stewart F A, Baas P, Photochem Photobiol 2006 Jul. 1).

All these treatments are used for small, superficial and not recurrent BCC, but are not indicated for nodular, cystic, infiltrative and morphoeic variants. Irradiation by photons has been used to deliver doses ranging from 20 to 73 Gy, in single or multiple treatments of BCC. The 5-year local control rate for recurrent Stage I and II carcinomas was 95%. (Wilder R B, Kittelson J M, Shimm D S., Cancer 1991; 68:2134-37). These results suggested that high cure rates can be obtained in basal cell carcinomas treated with radiation therapy, with cure rates comparable to Mohs micrographic surgery, which in these tumors is generally considered the "golden standard" treatment. Irradiation by conventional methods (radiotherapy by external beam X-rays or gamma rays), due to the penetrating nature of the photons, however, cannot be recommended for treatment of tumors in areas in which radiation can be very harmful (face, eyes), and has proven itself unsatisfactory in the treatment of SCC. The interstitial brachytherapy with needles or seeds of $^{192}$Ir has been employed in cases of SCC of the penis (T1, T2 and T3, and also in the carcinoma in-situ). The results significantly change with tumor grade; the preservation of the penis after 5 years has been 86% of all treated cases.

Radioactive sources in thin layer as used in e.g. brachytherapy are usually obtained by electrolytic deposition of a radioactive element on a metallic substrate. In such sources, the distribution of the radioactivity on the substrate material must be uniform, in order to impart a homogeneous dose rate from the surface of the source. The sources are generally used in the calibration of instruments for the measurement of the radioactivity of surfaces, but can also be used in the radiotherapy of superficial tumors. In the past, radioactive sources, in the form of metallic plaques containing the emitters $^{106}$Ru or $^{90}$Sr, have been used in the brachytherapy of ocular melanoma (Anteby et al., Ann Ophtamol, 1993, 25(9):339-41).

WO 2005/079757 discloses a method in which a radioisotope is mixed and/or reacted with a thermogelling biodegradable polymer, obtaining a product that can be applied directly inside a body tissue. to a tumor site, after surgical excision of the tumor mass, to destroy vestigial cancerous cells. The polymer should be injected into the body, and the obtained material must in all respect be classified as a radiopharmaceutical product. Consequently the attention of the inventors is strictly directed to the obtainment of a biodegradable, non-toxic, chelating polymer for intra-corporeal injective application, consisting in various combinations of fibrin, polypeptides, polyethylene-glycol blocks, biodegradable polyester blocks, as explicitly disclosed in the appended claims of WO 2005/079757. In the description or claims, however, brachytherapy treatment of skin tumors is not mentioned.

In U.S. Pat. No. 7,192,395 a method is disclosed in which a polymer is used as carrier of radioisotope in the preparation of radioactive balloons or wires. The document describes the coating of different material with polymers that have the ability to chelate different radioactive ions, and is aimed to obtain radioactive balloons for medical use, to be used in brachytherapy post-transluminal coronary angioplasty. While in the description of U.S. Pat. No. 7,192,395 a series of experiments on the chelation of ions on polymers, and an exposition of the general methods for the coating of plastic material by radioactive isotope ions are reported, the treatment of skin tumors is not mentioned, the attention being rather directed to the obtainment of non-toxic, chelating films, with low leaching of free radioisotope ions, to be used in the blood stream. Consequently, U.S. Pat. No. 7,192,395 is exclusively aimed to the intra-corporeal application of post-transluminal angioplasty brachytherapy, as clearly disclosed in the appended claims of the document.

In WO 99/42177 a radioactive stent is described, aimed to prevent restenosis by performing a brachytherapy after the endoluminal insertion of said stent apparatus. In order to render the stent radioactive, a layer of radioactive ions is deposited on the surface of the metallic stent. While a general description of the possible materials and methods for covering a metallic item with a radioactive polymer is presented in WO 99/42177, the treatment of skin tumors is not mentioned. The attention of this document is essentially focused and directed to the obtainment of a biocompatible cover radioactive polymer for a fixed metallic item (stent), to be used in an intra-corporeal application of post-transluminal angioplasty brachytherapy, as clearly disclosed in the appended claims of the document.

In U.S. Pat. No. 6,394,945 a radioactively coated substrate, and some methods for producing radioactive coatings on such substrates, are described. More specifically, this invention embraces the coating of implantable medical devices such as stents, catheters, radioactive seeds and the like for use in medical treatments with radioactive isotopes. While the invention relates to a method of producing a uniform permanent, distribution of radioisotope on a surface of a medical device, by using electroplating, the treatment of skin tumors by direct application on the patient is not mentioned, the attention being rather directed to the obtainment of medical device covered with radioisotopes, as clearly disclosed in the appended claims of the document.

In US 2007/265485 a device and method for localized delivery of beta radiation in surgical procedures, particularly ophthalmic procedures, is described, in which a localized delivery of beta radiation to treat Age Related Macular Degeneration is performed. The proposed device delivers beta radiation to the affected sub-macular region, and the device includes a radiotherapy emitting material positioned on the distal end or portion of the device, such as a shielded bent cannula. Also in this case in the description or claims of US 2007/265485, the brachytherapy treatment of skin tumors is not mentioned. The attention of the description is exclusively directed to the obtainment of a shielded, fixed, medical device, containing a radioactive isotope, to be used as a classical brachytherapy apparatus in ocular pathologies, as clearly disclosed in the appended claims of the document.

In US 2007/053830 a method of manufacture, treatment and compositions for an implant which permits localized delivery of labelling agents for therapy and diagnosis is disclosed. The labelling agent is a radioactive isotope for radiotherapy, incorporated into bioresorbable particulates with minimal leakage of the radioisotope. Therefore, one aspect of the application provides a biocompatible implant material which is resorbable, yet retains its chemical and physical integrity for a desired length of time, while a radioisotope or combination of radioisotopes is retained at a desired site, e.g. localized when implanted into the body of a patient. A particular embodiment relates to a radioactive resorbable implant material for localized radiotherapy, or radioembolization containing a resorbable base glass matrix in form of microspheres or fibers, with surface being of great chemical durability in human body fluids. The resorbable materials are used for localized radiotherapy through injection or surgical procedures. The material has to be injected into the body; consequently the attention of the inventors is strictly directed to the obtainment of a non-toxic material for intra-corporeal infective application, as explicitly disclosed in the appended claims of the document. In the description or claims of US 2007/053830, the brachytherapy treatment of skin tumors is not mentioned, and, consequently, no attention is focused on the medical methods and procedures for a selective irradiation of skin tumors.

In the case of skin tumors, the radiotherapy shows the premises for excellent cure rates, but drawbacks of external beam classical radiotherapy techniques strongly lower the clinical effectiveness; in such tumors an external irradiation selectively imparting a localized dose only to the cancer lesions, by sparing the healthy tissue, i.e. a topical administration of a radiation therapeutic dose, only directed to the skin tumor lesions, should be highly desirable. Therefore, an object of the present invention is to provide an improved radiotherapy method for treating skin tumors.

BRIEF SUMMARY

The object of the present invention is solved by a method of treating a skin lesion of a subject by epidermal radioisotope therapy, comprising the following steps in the following order:
(a) defining, and preferably marking, an area of skin to be treated;
(b) covering said area with a protective layer;
(c) applying a tailor-made radioactive source by applying a layer of a radioactive source material on said protective layer, such that said area is covered by said material while any area of skin not to be treated is spared;
(d) removing the radioactive source after a predetermined time period of irradiation.

In one embodiment, the skin lesion is a cancerous or non-cancerous lesion, preferably a cancerous lesion, more preferably selected from the group consisting of a basal cell carcinoma BCC, a squamous cell carcinoma SCC, an actinic keratosis and a cheloid (keloid).

In one embodiment, the area of skin to be treated is from less than 1 cm$^2$ up to 200 cm$^2$.

In one embodiment, the protective layer is a protective film or a protective foil.

In one embodiment, the protective film is formed by spreading a layer of a cream, a gel or a foam, preferably at about 10 µl/cm$^2$.

In one embodiment, the protective foil comprises a plastic material, e.g. is a thin plastic foil.

In one embodiment, the cream, the gel, the foam or the foil comprises one or more hydrophilic components.

In one embodiment, the protective film or foil has a thickness of from 20 to 60 µm.

In one embodiment, the radioactive source material comprises a matrix-forming component and a radioactive isotope, the radioactive isotope preferably being homogeneously distributed in the matrix-forming component.

In one embodiment, the radioactive source material is moldable.

In one embodiment, the layer of radioactive source material has a regular and uniform thickness.

In one embodiment, the matrix-forming component provides for a semi-fluid or fluid radioactive source material when being applied. Preferably, the matrix-forming component solidifies after applying.

In one embodiment, the matrix-forming component of the radioactive source material is a semi-fluid resin or paint, preferably a water soluble acrylic paint.

In one embodiment, the main constituent of the water soluble acrylic paint is an acrylic polymer emulsion.

In one embodiment, the water soluble acrylic paint comprises one or more additives selected from the group consisting of thickeners, surfactants, adhesion promoters, preservatives, defoamers, pH modifiers, dispersants, and plasticizers.

In one embodiment, the radioactive isotope is a beta emitter isotope, preferably selected from the group consisting of $^{188}$Re, $^{90}$Y and $^{177}$Lu.

In one embodiment, the radioactive isotope is a highly dispersed precipitate, and preferably is in the form of an insoluble microcolloid or nanocolloid.

In one embodiment, the radioactive isotope, when added to the matrix-forming component in order to prepare the radioactive source material, is in solution or in solid dispersion. Preferably, the radioactive isotope, when added to the matrix-forming component, is in highly dispersed solid form.

In one embodiment, the radioactive source material is applied to the area of skin to be treated, preferably by spreading, at an amount of from 2 to 50 μl/cm$^2$, preferably from 5 to 15 μl/cm$^2$.

In one embodiment, step (c) is repeated once, twice or several-fold. Thus, at least one further layer of a radioactive source material is spread such that the area of skin to be treated is covered by said material. Preferably, the further layer is spread after the underlying layer has been solidified. Thus, the radioactive source may be composed of more than one layer of radioactive source material.

In one embodiment, the predetermined time period of irradiation is from 10 minutes to three hours, preferably from 10 minutes to two hours, more preferably from 10 minutes to one our, most preferably from one to two hours.

In one embodiment, the method comprises the step of visually marking the area of skin to be treated, preferably by a demographic pen.

In one embodiment, the method further comprises the step of calculating the area of skin to be treated.

In one embodiment, the method further comprises the step of calculating, i.e. accurately calculating, the radiation dose to be delivered. For this purpose, a dosimetric plan is consulted and a dose-distribution curve is calculated using a numerical calculation method.

In one embodiment, the method further comprises the step of calculating, i.e. accurately calculating, the radiation dose distribution curve to be delivered using a dosimetric program or an algorithm.

In one embodiment, the method further comprises the step of pre-treating the skin lesion and/or area of skin to be treated, e.g. by cleaning, curettage, local anaesthesia, or provision of haemostasis.

In one embodiment, the method is repeated at least once. Multiple treatments, e.g. three, are also considered therapeutically valid and acceptable.

In one embodiment, the subject is a vertebrate, preferably a mammal, most preferably a human. In one embodiment, the subject is a patient.

In one embodiment, the skin lesion is located at a part of a body of the subject selected from the group consisting of face, nose, an ear, an eyelid, a lip, penis, and vulva.

In addition to the method described herein, auxiliary equipment for carrying out the method as well as a therapeutic kit comprising such auxiliary equipment is considered.

An "epidermal radioisotope therapy" is a specialized type of brachytherapy.

The "area of skin to be treated" usually encompasses a skin lesion, e.g. in case of a carcinoma both the area of evident tumor cell infiltration and an area in which a neoangiogenic development is observed, and a border of some mm, preferably 1-10 mm, more preferably 2-3 mm, of apparently healthy tissue surrounding the skin lesion.

The "protective film" advantageously is uniform and continuous and easily adheres to the surface of the area of skin to be treated. This film protects the subject from any possible radioactive contamination and from any physical contact with the radioactive source. By such a film, irradiation of the skin lesion can be performed without physically touching the skin of the patient with any radioactive source material.

The "protective foil" also adheres to the surface of the area of skin to be treated and protects the subject from radioactive contamination and physical contact with the radioactive source. Usually, it is a thin plastic foil which is directly applied to the area of skin to be treated to protect and insulate the skin.

A "tailor-made radioactive source" as used herein refers to a source which is adapted to an individual or unique area of skin to be treated. The source is moldable and can adapt different shapes and thickness.

Here, a medical application of radioactive sources useful for radiotherapy of skin tumors in human and animals is provided. To our knowledge, none prior-art document discloses a medical method, aimed or directed to the therapy of skin tumors by shaping a selective, individually tailor-made brachytherapy source for the irradiation of the cancerous lesions. In the present proposed method, differently from the sources currently used in classical brachytherapy with metallic radioactive plaques or seeds or needles, the obtained sources are moldable, to assume different shapes and thicknesses, and can be safely used without contamination of the physician and the patient. By starting from a solution containing a radioactive isotope, a solid matrix is obtained, in which the radioactive isotope is embedded; the matrix in which the isotope is immobilized is sufficiently flexible and variable to adapt to different surfaces and substrates. The matrix which encloses the radioactive isotope is chosen in order to be chemically compatible with the embedded isotope, and to ensure homogeneity of the imparted dose. The radioactive sources obtained in this way can be safely and effectively used in the therapy of skin tumors, with excellent cure rate and with negligible side effects.

The classic gamma brachytherapy requires complex programs of treatment planning and calculation of dose distribution, in order to obtain an individually adjusted dose distribution, In spite of the complexity of calculations and irradiation apparatus, the dose distribution is far from ideal, due to the penetrating nature of the photons, and a large number of sessions (30-40) are usually required for a complete treatment.

In this respect, the use of beta radiation isotopes embedded in a tailor-made irradiation mold, like the technique proposed in the present application, can override, in skin tumors, the drawbacks of classical radiotherapy or brachytherapy, which make use for irradiation of gamma or X-rays photons. By using for therapeutic treatments a tailor-made source, like the ones proposed and realized in the present application, not only the margin of irradiation can be easily controlled by the application of the resin only on the lesion area, but the dose distribution curve obtained by beta particles, almost ideally follows the typical distribution of the tumor invasion in the dermal tissue. This fact allows an administration of therapeutic doses only at the required depth, without unnecessary dose deposition in the sub dermal tissue, independently from the lesion shape complexity, and from the number of the lesions. The product can be easily applied on the protected skin, always obtaining a regular and smooth surface of uniform thickness. The protection of the skin by a thin layer of an accurately calculated amount of protective cream, chosen in the group of creams or gels containing one or more hydrophilic components, or by a layer of a thin plastic adherent foil applied to the lesion, was important to prevent any possible skin contamination.

Moreover, by using the described method, the material of the radioactive source doesn't in any way touch the skin, and the sources are not classified as radiopharmaceutical products. The total dose imparted from the beta emitting layer depends on the amount of radioactive nanocolloid; the mass unitary dose depends on the ratio (radioactivity of colloid)/(weight of resin); the unitary surface dose depends on the ratio (radioactivity of colloid)/(area of applied resin). The amount of resin necessary to a uniform spreading is approximately 10 microliters/square cm ($\mu l/cm^2$). The thickness of the resin must be taken into account in the dosimetric program for a precise dose evaluation, by calculating the self-absorption effect.

BRIEF DESCRIPTION OF DRAWINGS

FIG. 1 schematically shows an exploded view of a section of a skin, showing a marked area 2 of skin 1 to be treated, a protective layer 3 on the skin 1, and a layer 4 of a radioactive source applied on the protective layer 3.

DETAILED DISCLOSURE

In the following the invention will be described in more detail with reference to the examples. While the descriptions here reported refer to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive, the scope of the invention being indicated by the appended claims rather than the foregoing description. All changes that come within the meaning of and range of equivalency of the claims are therefore intended to be embraced therein.

EXAMPLE 1

Composition and Methods for the Fabrication of Radioactive Sources for Radiotherapy of Skin Tumors Among the possible modes for obtaining radioactive sources in thin layer, a useful technique consists in evaporating a volatile solution, containing both a coordination complex of the isotope and a dissolved matrix-forming molecule (i.e. a plastic, or a gum, or a polymer). By this technique, however, a uniformity of dispersion of the isotope during the solvent evaporation is hard to obtain, due to the fact that the evaporation of a solvent is not a regular process. Another technique used consists in the use of a polymerizable matrix (epoxy resin, etc.); in this case the semi-solid form of the matrix renders problematic the fabrication of a regular thin layer of uniform thickness.

The present application proposes as a matrix for the preparation of radioactive source in thin layer for use in medicine, the use, as a binding matrix, of a semi-fluid resin or paint, preferably chosen in the group of water soluble acrylic paints. Acrylic paint is fast-drying paint, and is a chemically complex mixture, whose main component basically consists in an acrylic polymer emulsion; it also contains variable amounts of thickeners, surfactants, adhesion promoters, preservatives, defoamers, pH modifiers, dispersants, plasticizers. Acrylic paints can be diluted with water, but become water-resistant when dry. Depending on the dilution degree, the finished acrylic painting can resemble a water-color or an oil painting, or have its own unique characteristics, not attainable with the other products. Acrylic paints have very good adhesive qualities, and are very stable; they resist oxidization and chemical decomposition, and do not yellow over time. Their water-solubility allows for easier clean-up and reduces the need to use chemicals that may create harmful fumes; the material is non toxic and doesn't include in its composition volatile organic solvents. Acrylic paint is also very adhesive and flexible by nature, and can be used on a wide variety of surfaces.

The radioactive isotope can be added to the acrylic paint both in solution and in solid form; the addition of an isotope in solid form is preferred, due to a lesser probability of contamination, for the physician and for the patient, during the preparation of the source, and during the application of the source on the skin of the patient. In order to obtain a good homogeneity of the source the added solid should be in a highly dispersed form, like in the form of a micro or of a nano precipitate.

The radioactive isotope that can be added to the acrylic paint can be an alpha, a beta or a gamma emitter. An alpha emitter has a range for dose deposition curve in human tissue lower lesser than 1 mm, distance that is too short to completely reach the depth of most common skin tumors (1-5 mm). A gamma emitter has a dose deposition in human tissue too deep, due to the highly penetrating nature of the photons, and could impart a non-negligible doses to underlying tissue, so arising the possibility of long term after effects on healthy tissue. The use of a beta radiation isotopes added to the acrylic paint represents the best solution for the brachytherapy of skin tumors; as a matter of fact the electrons from high energy (>1 MeV) beta emitters isotopes deposit more than 90% of the dose to the first few mm of the skin, which is the depth usually interested from tumor invasion, but is able to spare from irradiation the deeper dermal tissue.

1.1 First Example of Preparation of a Radioactive Source for Radiotherapy

Carrier-free $^{188}$Re as perrhenate was obtained from a $^{188}$W/$^{188}$Re generator by elution with saline; the isotope was added to a kit containing 250 mg of thioacetamide, 1 mg of $NH_4ReO_4$, 1 mg of polyvinylpyrrolidone, 100 microliters of conc. HCl, and the solution was heated to 90° C. for 30 minutes. A nanocolloid (typically 200-800 nm) of Rhenium sulphide was obtained; the precipitate was centrifuged and doubly washed by saline, again centrifuged and thoroughly mixed with a synthetic acrylic resin in a test tube, in order to obtain a completely homogeneous distribution of the radioactive $^{188}$Re. The radioactivity of the test tube was measured, and the homogeneity in different fractions of the resin was found better than 98%.

1.2. Second Example of Preparation of a Radioactive Source for Radiotherapy

Carrier-added beta emitter isotope $^{32}$P was commercially obtained in the form of sodium phosphate; to 1 ml of the radioactive isotope solution, 1 ml of a 1M solution of $BaCl_2$ and 0.1 ml of a 1M solution of $NH_4OH$ were added. A precipitate of barium phosphate was formed at room temperature, which was successively centrifuged and doubly washed by saline, again centrifuged and thoroughly mixed with a synthetic acrylic resin in a test tube, in order to obtain a completely homogeneous distribution of the radioactive $^{32}$P. The radioactivity of the test tube was measured, and the homogeneity in different fractions of the resin was found better than 98%.

For homogeneity quality control, a uniform distribution of radioactive $^{188}$Re nanocolloid in acrylic resin was obtained, by following the procedure reported in Example 1. A circular source, 1 cm diameter, was prepared by painting the radioactive resin on a solid support. The radioactivity surface distribution of the obtained source was measured by using a phosphor storage screen (Cyclone—Perkin Elmer), in which the integrated density of the screen is proportional to absorbed dose. The source was put in contact with the active screen for a fixed time, interposing between source and screen one or more plastic sheets, each 100 micron thickness, in order to obtain information about the source homogeneity, and the dose distribution curve of beta particles of $^{188}$Re vs depth. The surface homogeneity of the source was found better than 98%. The dose distribution curve obtained by interposing the absorbers between the source and the phosphor storage screen was compared with Montecarlo calculation (EGS4), and with multi-point source calculation. The correlation coefficient between the measured values, and the two above mentioned models was found, respectively, 0.97 and 0.96.

EXAMPLE 2

Application of the Radiotherapy of Skin Tumors

More than 300 patients with histologically confirmed diagnosis of BCC or of SCC were enrolled for a brachytherapy treatment, by using the radioactive sources prepared by one of the above mentioned methods. In many of the patients a relapse of the tumor successive to a surgical excision was present; in others a surgical operation would have been impossible, or functionally and/or aesthetically unacceptable. The application of the product must be preceded by an accurate cleaning and curettage of the lesions. This treatment is useful not only for more precisely delineating the extent of a tumor, but also to eliminate all the keratinic crusts, granulation tissue, scabs, that, due to their thickness, would stop the beta particles irradiation. Both BCC and SCC appear often ulcerated, with presence of serous and blood scabs; in other cases keratin plaques or nodules of horny consistence are present. In all cases an accurate and complete elimination must be performed. A softening of the scab with saline helps in the removing; in some cases, like vulva or penis lesions, a local anaesthesia before removing is advisable. If, after the removal of the scab, an haemorrhage arise, an haemostatic agent must be applied on the lesion, to stop the bleeding; an haemostatic gauze with oxidized cellulose applied for some minutes works well, in most of the cases.

The area to be treated is outlined by using accurate visual examination and dermoscopy epiluminescence; the irradiation usually includes both the area of evident infiltration, and the area in which a neoangiogenic development is present; a border of some mm of apparently health tissue around the lesion is also usually included in the irradiation area, especially if a possible invasion is suspected. The clinical practice has showed that a border of two to three mm beyond the visible invasion and neoangiogenic development is sufficient to assure a selective irradiation in most cases. The surface to be treated is outlined by a dermograhic pen, and the drawing is transferred on a transparent thin plastic sheet settled on the lesion. A simple and effective method for the determination of the area is performed by laying down the transparent sheet on a graphing or millimetre paper, and counting the square millimetres inside the outlined area.

The whole surface of the skin to be treated is protected by uniformly and rapidly spreading it with a layer of a special gel cream, chosen in a group of creams or gels containing one or more hydrophilic components, about 10 microliters/square cm ($\mu l/cm^2$), in order to prevent a possible radioactive contamination of the epidermis from the radioactive matrix. The gel rapidly desiccates, leaving an adhering, uniform and continuous protection film, with typical final thickness of 30-40 microns ($\mu m$). A second system for the protection and insulation of the skin is to apply a medical spray, like typically a liquid plaster, and then to put on the lesion a thin adaptable plastic foil, typically 3-60 microns ($\mu m$) in thickness.

The radioactive resin is applied above the protective cream or plastic foil layer, by using a specially designed shielded medical applicator. The resin has a uniformly distributed and certified radioactivity, and must be applied as accurately and homogeneously as possible, by covering all the previously outlined area. After some minutes the resin becomes solid, without any appreciable shrinkage; the radioactive mold is kept on the lesion for the time necessary to impart the calculated dose distribution. At the edge of the lesion, a border of apparently healthy tissue of some mm was also included in the irradiation area, in order to deposit a homogeneous dose to the tumor cell of the external edge of the lesion.

The activity of the beta emitter isotopes used in the treatments range from 1 mCi in the smaller lesions, up to more than 50 mCi in larger lesions; $^{90}$Y, $^{32}$P and $^{166}$Ho have been used in some cases, but in 90% of the patients $^{188}$Re was used, due to the superior irradiation properties, availability and favourable chemistry of this isotope. The resin and cream thickness are taken into account into an accurate real-time dosimetric calculation, for the beta particles absorption effect. For each lesion, the dose distribution only depends from the initial radioactivity, surface of the lesion and contact time.

The radioactive source application procedure requires a time of 10-120 seconds per patient, while typical irradiation time per session is less than one hour. For each patient and for each lesion, the dose-distribution curve is calculated, by using a point source numerical calculation method, previously validated vs a dose deposition Montecarlo program. Clinical practice has demonstrated that mean doses of 40-60 Gy to depths of 300-600 microns from the epidermis (the exact value depending on histological indications and site of the tumor) are effective for high cure rates. A dose of 50 Gy to 300 microns has been used in lesion of genitals, lips and mouth; a dose of 50 Gy to 400 or 500 microns was the standard dose used for most of the BCC and SCC lesions; a dose of 50 Gy to 600 microns was the dose used in thick tumors.

At the end of the irradiation, the resin is removed from the skin by using a specially designed tongs shielded remover. The resin, which doesn't adhere to the skin, due to the presence of the cream or of the thin plastic foil on the skin lesion, is easily and completely removed in one piece, and is safely discarded, without any measurable contamination of the skin of the patient, and without appreciable irradiation for the medical personnel.

EXAMPLE 3

Medical Results

Immediately after the treatment, a faint reddening of the treated skin area is visible. After a few days a variable erythema is present, sometimes with emission of serum, and a crust or scab is formed. An apparent worsening of the aspect of the lesion is often observed, with the appearance of a burn, but the bleeding, often present before the therapy, usually disappears. After 40-120 days the erythema fades, sometimes a second scab is formed, and itch is present. The clinical healing is more clearly apparent, the tumor neoangiogenic development, often clearly visible with epiluminescence before the treatment, starts to disappear. After 60-180 days, in most of the cases, an apparent clinical healing is present, rarely with persistence of a scab. The lesion area becomes paler than the untreated skin, the tumor neoangiogenic development disappears, and a fading in the skin coloration appears.

A Perspex screen 10 mm thick was found sufficient to protect the physician face from β radiation during the phase of product application to the patient, typically lasting from 10 to 120 seconds. During the irradiation, typically lasting from 15 min to 1 hour, the patient is kept isolated in a medical room. If an irradiation on the nose, or near the eye, is performed, the patient wears a pair of lead or polymethylmethacrylate spectacles, for crystalline protection.

After the required irradiation time, a radioactivity test is performed on the treated lesion; in all cases a total absence of any measurable contamination has been always demonstrated. More than 300 patients (for a total of more than 1000 lesions) with histologically or clinically confirmed diagnosis of BCC and of SCC have been up today successfully treated. The treated areas rated from less than 1 cm$^2$ up to 70 cm$^2$ per lesion. In all treated cases, an apparent clinical remission occurred after 3-6 months; a complete response was obtained in 98.8% of the treated cases, in 89% of the cases after a single application. In 11% of the patients two to three treatments were applied. In half of these cases the second treatment was applied on lesion contiguous to the treated area, or to the border of the previously treated lesions; in such cases the evaluation of the area interested from the tumor invasion has been likely underestimated. In other cases, thicker tumors generally required two or even three treatments (i.e. keratoacanthoma, or thick nodular BCC), as was easily foreseen by purely dosimetric consideration. In a limited number of cases multiple treatments (maximum three) on the same area have been found necessary for a complete healing; possible reasons should be a greater radio-resistance of the tumor cell line, or a protective effect of the melanin (pigmented BCC). Neither unaesthetic scars, nor side effects, were never observed. After a follow up of 15-82 months, no signs of clinical relapses were present in any of the treated patients. When a histological examination was performed, a complete tumor regression was observed.

The results obtained by using the described product and technique can be considered quite satisfactory for the great majority of treated patients, and is proposed as a new therapeutic choice, not only alternative to medical treatments, but also to surgery. Its main advantage lies in the usefulness in all types of BCC and SCC, without restriction of site, dimension, clinical or histological type, and patient clinical situation. A superiority of the proposed treatment with respect to the surgery is evident for all the tumors located in high-risk areas, or difficult sites on which surgery would be difficult (nose, ears, eyelids), in the patients with a high number of lesions or with tumor relapses, in patients in which surgery would produce functional mutilations (penis, vulva, eyelids lesions), and, generally, in older, infirm, or otherwise inoperable patients. Avoidance of scarring and of suboptimal cosmetic outcome were also considered by patients an important decision factor in the choice of therapeutic path. The proposed technique is a rapid, safe, treatment, mostly performed in a single therapeutic session, without discomfort for the patient, and offers a complete aesthetical and functional restitutio ad integrum.

We claim:

1. A method of treating a skin lesion of a subject by epidermal radioisotope therapy, comprising:
    (a) defining an area of skin, of a subject, to be treated;
    (b) subsequent to (a), covering the area of skin to be treated with a protective layer;
    (c) subsequent to (b), spreading a moldable radioactive source material on the protective layer over the area of skin to be treated so as to create a layer of the moldable radioactive source material over the area of the skin to be treated, such that the moldable radioactive source material is not over any area of skin, of the subject, not to be treated,
    wherein the moldable radioactive source material comprises a semi-fluid or fluid radioactive source material when spreading the moldable radioactive source material on the protective layer over the area of skin to be treated so as to create a layer of the moldable radioactive source material over the area of the skin to be treated,
    wherein the moldable radioactive source material comprises a radioactive source,
    wherein irradiation from the radioactive source treats a skin lesion, of the subject, and
    wherein the protective layer prevents physical contact between the moldable radioactive source material spread on the protective layer and the area of skin to be treated covered by the protective layer; and
    (d) removing the moldable radioactive source material after a predetermined time period of irradiation.

2. The method according to claim 1,
wherein the skin lesion is a cancerous lesion.

3. The method according to claim 2,
wherein the skin lesion is selected from the group consisting of:
    a basal cell carcinoma BCC, a squamous cell carcinoma SCC, an actinic keratosis, and a cheloid.

4. The method according to claim 1,
wherein the area of skin to be treated is from less than 1 cm$^2$ up to 200 cm$^2$.

5. The method according to claim 1,
wherein the protective layer is a protective foil comprising a plastic material.

6. The method according to claim 5,
wherein the protective foil comprises one or more hydrophilic components.

7. The method according to claim 5,
wherein the protective foil has a thickness of from 20 to 60 μm.

8. The method according to claim 1,
wherein the moldable radioactive source material comprises a matrix-forming component and a radioactive isotope.

9. The method according to claim 8,
wherein the matrix-forming component is a semi-fluid resin or paint.

10. The method according to claim 8,
wherein the radioactive isotope is a beta emitter isotope.

11. The method according to claim 8,
wherein the radioactive isotope is in the form of an insoluble microcolloid or nanocolloid.

12. The method according to claim 8,
wherein the radioactive isotope is homogeneously distributed in the matrix-forming component.

13. The method according to claim 8,
wherein the matrix-forming component is a water soluble acrylic paint.

14. The method according to claim 8,
wherein the radioactive isotope is selected from the group consisting of:
$^{188}$Re, $^{90}$Y, and $^{177}$Lu.

15. The method according to claim 1,
wherein spreading the moldable radioactive source material on the protective layer over the area of skin to be treated comprises spreading the moldable radioactive source material on the protective layer over the area of skin to be treated at an amount of from 2 to 50 µl/cm².

16. The method according to claim 1,
wherein the predetermined time period of irradiation is from 10 minutes to three hours.

17. The method according to claim 1, further comprising:
calculating a radiation dose distribution curve to be delivered using a dosimetric program or an algorithm.

18. The method according to claim 1,
wherein the skin lesion is located at a part of a body of the subject, and
wherein the part of the body of the subject is selected from the group consisting of:
a face, a nose, an ear, an eyelid, a lip, a penis, and a vulva.

19. The method according to claim 1,
wherein spreading the moldable radioactive source material on the protective layer over the area of skin to be treated comprises spreading the moldable radioactive source material on the protective layer over the area of skin to be treated at an amount from 5 to 15 µl/cm².

20. The method according to claim 1,
wherein the predetermined time period of irradiation is from one to two hours.

21. The method according to claim 1,
wherein the subject is a mammal.

22. The method according to claim 1,
wherein the subject is a human.

23. The method according to claim 1,
wherein the skin lesion is a non-cancerous lesion.

24. The method according to claim 1,
wherein the layer of the moldable radioactive source material over the area of the skin to be treated has a uniform thickness.

25. A method of treating a skin lesion of a subject by epidermal radioisotope therapy, comprising:
(a) defining an area of skin, of a subject, to be treated;
(b) covering the area of skin to be treated with a protective layer,
wherein the protective layer is a protective film formed by spreading a layer of a cream, a gel, or a foam;
(c) spreading a moldable radioactive source material on the protective layer over the area of skin to be treated so as to create a layer of the moldable radioactive source material over the area of the skin to be treated, such that the moldable radioactive source material is not over any area of skin, of the subject, not to be treated,
wherein the moldable radioactive source material comprises a semi-fluid or fluid radioactive source material when spreading the moldable radioactive source material on the protective layer over the area of skin to be treated so as to create a layer of the moldable radioactive source material over the area of the skin to be treated,
wherein the moldable radioactive source material comprises a radioactive source,
wherein irradiation from the radioactive source treats a skin lesion, of the subject, and
wherein the protective layer prevents physical contact between the moldable radioactive source material spread on the protective layer and the area of skin to be treated covered by the protective layer; and
(d) removing the moldable radioactive source material after a predetermined time period of irradiation.

26. The method according to claim 25,
wherein the cream, the gel, or the foam comprises one or more hydrophilic components.

27. The method according to claim 25,
wherein the protective film has a thickness of from 20 to 60 µm.

28. A method of treating a skin lesion of a subject by epidermal radioisotope therapy, comprising:
(a) defining an area of skin, of a subject, to be treated;
(b) covering the area of skin to be treated with a protective layer;
(c) spreading a moldable radioactive source material on the protective layer over the area of skin to be treated so as to create a layer of the moldable radioactive source material over the area of the skin to be treated, such that the moldable radioactive source material is not over any area of skin, of the subject, not to be treated,
wherein the moldable radioactive source material comprises a radioactive source,
wherein the moldable radioactive source material comprises a matrix-forming component and a radioactive isotope,
wherein the matrix-forming component provides for a semi-fluid or fluid radioactive source material when spreading the moldable radioactive source material on the protective layer over the area of skin to be treated so as to create a layer of the moldable radioactive source material over the area of the skin to be treated,
wherein irradiation from the radioactive source treats a skin lesion, of the subject, and
wherein the protective layer prevents physical contact between the moldable radioactive source material spread on the protective layer and the area of skin to be treated covered by the protective layer; and
(d) removing the moldable radioactive source material after a predetermined time period of irradiation.

29. The method according to claim 28,
wherein after spreading the moldable radioactive source material on the protective layer over the area of skin to be treated so as to create a layer of the moldable radioactive source material over the area of the skin to be treated, the layer of the moldable radioactive source material solidifies.

30. A method of treating a skin lesion of a subject by epidermal radioisotope therapy, comprising:
(a) defining an area of skin, of a subject, to be treated;
(b) covering the area of skin to be treated with a protective layer;
(c) subsequent to (b), spreading a moldable radioactive source material on the protective layer over the area of skin to be treated so as to create a layer of the moldable radioactive source material over the area of the skin to be treated, such that the moldable radioactive source material is not over any area of skin, of the subject, not to be treated,
wherein the moldable radioactive source material comprises a semi-fluid or fluid radioactive source material that solidifies after spreading the moldable radioactive source material on the protective layer over the area of skin to be treated, wherein the semi-fluid or fluid radioactive source material comprises a radioactive source, wherein irradiation from the radioactive source treats a skin lesion, of the subject, wherein the skin lesion is a tumor skin lesion, and wherein the protective layer prevents physical contact between the moldable radioactive source material spread on the protective layer and the area of skin to be treated covered by the protective layer; and (d) removing the moldable radioactive source material after a predetermined time period of irradiation.

* * * * *

UNITED STATES PATENT AND TRADEMARK OFFICE
CERTIFICATE OF CORRECTION

PATENT NO. : 9,486,642 B2  
APPLICATION NO. : 13/025703  
DATED : November 8, 2016  
INVENTOR(S) : Cesidio Cipriani and Maria Desantis Page 1 of 1

It is certified that error appears in the above-identified patent and that said Letters Patent is hereby corrected as shown below:

Column 2,
Line 14, "and. SCC" should read --and SCC--.

Column 3,
Line 12, "Mobs' technique" should read --Mohs' technique--.

Column 7,
Line 25, "demographic" should read --dermographic--.

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*